US010112022B2

(12) United States Patent
Knepper et al.

(10) Patent No.: US 10,112,022 B2
(45) Date of Patent: Oct. 30, 2018

(54) METHOD FOR DETECTING AN INSPIRATORY FLOW LIMITATION DURING SLEEP-DISORDERED BREATHING

(71) Applicant: DeVilbiss Healthcare LLC, Somerset, PA (US)

(72) Inventors: Michael B Knepper, Friedens, PA (US); Jeffrey J Lauer, Nanty Glo, PA (US)

(73) Assignee: DeVilbiss Healthcare LLC, Somerset, PA (US)

( * ) Notice: Subject to any disclaimer, the term of this patent is extended or adjusted under 35 U.S.C. 154(b) by 726 days.

(21) Appl. No.: 14/489,552

(22) Filed: Sep. 18, 2014

(65) Prior Publication Data

US 2016/0082210 A1    Mar. 24, 2016

(51) Int. Cl.
*A61M 16/00* (2006.01)
*A61B 5/087* (2006.01)
*A61B 5/00* (2006.01)

(52) U.S. Cl.
CPC ......... *A61M 16/0069* (2014.02); *A61B 5/087* (2013.01); *A61M 16/0051* (2013.01); *A61B 5/4836* (2013.01); *A61M 2016/0027* (2013.01); *A61M 2016/0036* (2013.01); *A61M 2205/52* (2013.01); *A61M 2230/46* (2013.01)

(58) Field of Classification Search
CPC ......... A61M 16/0069; A61M 16/0051; A61M 16/00; A61M 16/0021; A61M 16/0039; A61M 16/0036; A61M 2016/0069; A61M 2016/0027; A61M 2016/0036; A61M 2205/52; A61B 5/087; A61B 5/4836; A61B 5/7278; A61B 5/7282; A61B 5/726; A61B 5/7235; A61B 5/7239

See application file for complete search history.

(56) References Cited

U.S. PATENT DOCUMENTS

| 5,245,995 A | 9/1993 | Sullivan et al. |
| 5,335,654 A | 8/1994 | Rapoport |
| 5,483,969 A * | 1/1996 | Testerman ........... A61B 5/1135 600/529 |
| 5,490,502 A | 2/1996 | Rapoport |
| 5,546,933 A | 8/1996 | Rapoport |
| 5,546,952 A | 8/1996 | Erickson |
| 5,645,053 A | 7/1997 | Remmers et al. |
| 5,704,345 A | 1/1998 | Berthon-Jones |

(Continued)

FOREIGN PATENT DOCUMENTS

| EP | 2510966 A1 | 10/2012 |
| WO | 199718752 A1 | 5/1997 |

(Continued)

OTHER PUBLICATIONS

Analysis of Inspiratory Flow Shapes in Patients With Partial Upper-Airway Obstruction During Sleep, Aittokallio, et al, CHEST 2001; 119:37-44.

*Primary Examiner* — Gregory Anderson
*Assistant Examiner* — Margaret Luarca
(74) *Attorney, Agent, or Firm* — Carter, DeLuca, Farrell & Schmidt, LLP

(57) ABSTRACT

A feature implemented in a CPAP breathing therapy machine to determine if the patient is suffering from a flow limitation condition and if so, altering the operation of the CPAP machine to attempt to alleviate the condition.

18 Claims, 4 Drawing Sheets

(56) References Cited

U.S. PATENT DOCUMENTS

| | | | |
|---|---|---|---|
| 5,803,066 | A | 9/1998 | Rapoport et al. |
| 6,739,335 | B1 | 5/2004 | Rapport et al. |
| 6,814,073 | B2 | 11/2004 | Wickham |
| 7,013,893 | B2 | 3/2006 | Wickham |
| 7,159,588 | B2 | 1/2007 | Wickham |
| 7,722,546 | B2 | 5/2010 | Madaus et al. |
| 7,934,500 | B2 | 5/2011 | Madaus et al. |
| 8,020,555 | B2 | 9/2011 | Rapoport |
| 8,408,205 | B2 | 4/2013 | Madaus et al. |
| 8,413,654 | B2 | 4/2013 | Bateman |
| 8,607,793 | B2 | 12/2013 | Armitstead et al. |
| 2004/0123866 | A1 | 7/2004 | Berthon-Jones |
| 2005/0241639 | A1* | 11/2005 | Zilberg ............... A61B 5/0803 128/204.21 |
| 2006/0037614 | A1* | 2/2006 | Madaus ............... A61B 5/087 128/204.23 |
| 2007/0215146 | A1 | 9/2007 | Douglas et al. |
| 2008/0082018 | A1* | 4/2008 | Sackner ............... A61B 5/0476 600/538 |
| 2010/0056939 | A1* | 3/2010 | Tarassenko .......... A61B 5/0452 600/509 |
| 2010/0258124 | A1 | 10/2010 | Madaus et al. |
| 2012/0179061 | A1 | 7/2012 | Ramanan et al. |

FOREIGN PATENT DOCUMENTS

| | | | |
|---|---|---|---|
| WO | 2007101296 | A1 | 9/2007 |
| WO | 2012126041 | A1 | 9/2012 |

\* cited by examiner

METHOD FOR DETECTING AN INSPIRATORY FLOW LIMITATION DURING SLEEP-DISORDERED BREATHING

FIELD OF THE INVENTION

This invention relates generally to the field of breathing therapy machines of the type used to treat obstructive and/or central sleep disorders and specifically to the treatment of such sleep disorders when flow limited breathing patterns are detected.

BACKGROUND OF THE INVENTION

Continuous Positive Airways Pressure (CPAP) breathing therapy machines are well known in the art for use in the treatment of sleep disordered breathing by supplying a continuous positive pressure to a patient's airway while the patient sleeps. A typical CPAP apparatus is programmed with a therapy pressure, and is able to maintain the set pressure (measured either at the mask or at a base unit) during the inhalation and exhalation phases of the breathing cycle. The pressure setting is typically programmed via a control on the unit. Bi-PAP machines will typically vary the positive pressure delivered to the user during the inhalation and exhalation phases of the breathing cycle. Typically, Bi-PAP machines deliver a lower pressure during the exhalation phase of the breathing cycle, to make it easier or less uncomfortable for patients to exhale while using the machine. The Bi-PAP machine is typically programmed with a therapy pressure, which is used as the inhalation pressure, while the exhalation pressure is typically a standard difference from the inhalation pressure.

FIG. 1 shows a schematic view of a typical prior art CPAP/Bi-PAP machine 30. Positive pressure is maintained by regulated blower 40, under control of motor control circuitry 38. Blower 40 supplies a pressurized flow of air to a mask connected via the flexible tube (not shown) to blower 40. Regardless of whether the device is a CPAP machine or a Bi-PAP machine, microprocessor 34, in accordance with normal operating programming stored in memory 36 produces a motor control signal which is interpreted by motor control circuitry 38. Motor control circuitry 38 translates motor control signal 37 into electrical impulses that control the speed of blower 40 to produce the desired pressure through flow element 42 and ultimately to the user of the device. The machine may be equipped with various sensors, such as pressure sensor 44 and flow sensor 46 to aid in the detection of sleep events. Control and programming of the device is accomplished via user interface 32.

The term "inspiratory flow limitation" describes a physiological condition in which the respiratory pattern is defined by constant or decreasing air flow without pressure dependence throughout significant portions of inspiration. This flow limitation is commonly caused by a narrowing of the upper airway. The pattern can be identified by a flattening of areas of the inspiratory waveform, as detected in the CPAP patient interface, resulting in an inspiratory waveform contour having plateaus which correlate to an elevated upper airway resistance.

The ability to detect the flow limitation condition is important for several reasons. If the increased airway resistance is sufficiently high, the tidal volume will fall. If the high upper airway resistance and reduced tidal volume persist, sleep-disordered breathing events will likely occur in the form of hypopneas or even apneas. Furthermore, if sufficient inspiratory muscle effort is required to overcome the flow limitation, transient arousals from sleep may occur, which may lead to daytime somnolence. Titration studies have also shown that flow limitation may curtail periods of deep sleep, even when the patient is not aroused.

In the context of a CPAP breathing therapy device, the ability to reliably detect a flow limitation condition can be used as an aid in adjusting the therapy pressure. Typically, a breathing therapy machine will seek to deliver the lowest possible therapeutically effective pressure to the patient, such as to minimize any patient discomfort associated with the use of the device. Typically, such devices will slowly lower the therapy pressure until the patient experiences an event, then will raise the pressure to stop the events, and then will return to slowly lowering the pressure. The ability to detect flow limitations as the pressure is lowered can act as a warning mechanism that further lowering the pressure may precipitate the occurrence of events. Therefore, when the flow limitation condition is detected, the CPAP machine can stop the lowering of the pressure, or increase the pressure to alleviate the flow limitation condition.

There are many methods of detecting flow limitation extant in the literature and several have been implemented in prior art CPAP machines. However, it has been found that prior art methods are unreliable and may often miss detecting flow limitation conditions, particularly in situations where the airflow waveform does not exhibit well-defined plateau areas in the inspiratory portion of the waveform. Therefore it would be desirable to have a more reliable method of determining the flow limitation condition.

SUMMARY OF THE INVENTION

The present invention presents an improved method of detecting a flow limited breathing pattern in a CPAP device. In this method, the flow waveform for each breath is analyzed by calculating the variance in the average slope for a moving window across the data points of the waveform. The results of the calculation are then analyzed to determine if the slope at any point in the waveform is flat enough (i.e., has a low enough variance) to warrant a determination of possible flow limitation. In a second embodiment, an analysis of the duty cycle kinetics of the airflow waveform is used to add certainty to the determination of a flow limitation condition.

The CPAP machine can use the detection of a flow limitation condition to alter the therapy pressure delivered to the patient. The onset of the flow limitation condition can be a signal that further lowering of the therapeutic pressure may result in events, such as hypopneas or apneas. Thus, the machine can use this information to curtail the lowering of pressure, or to increase pressure if the flow limitation condition persists.

DETAILED DESCRIPTION OF THE INVENTION

Figure 1:
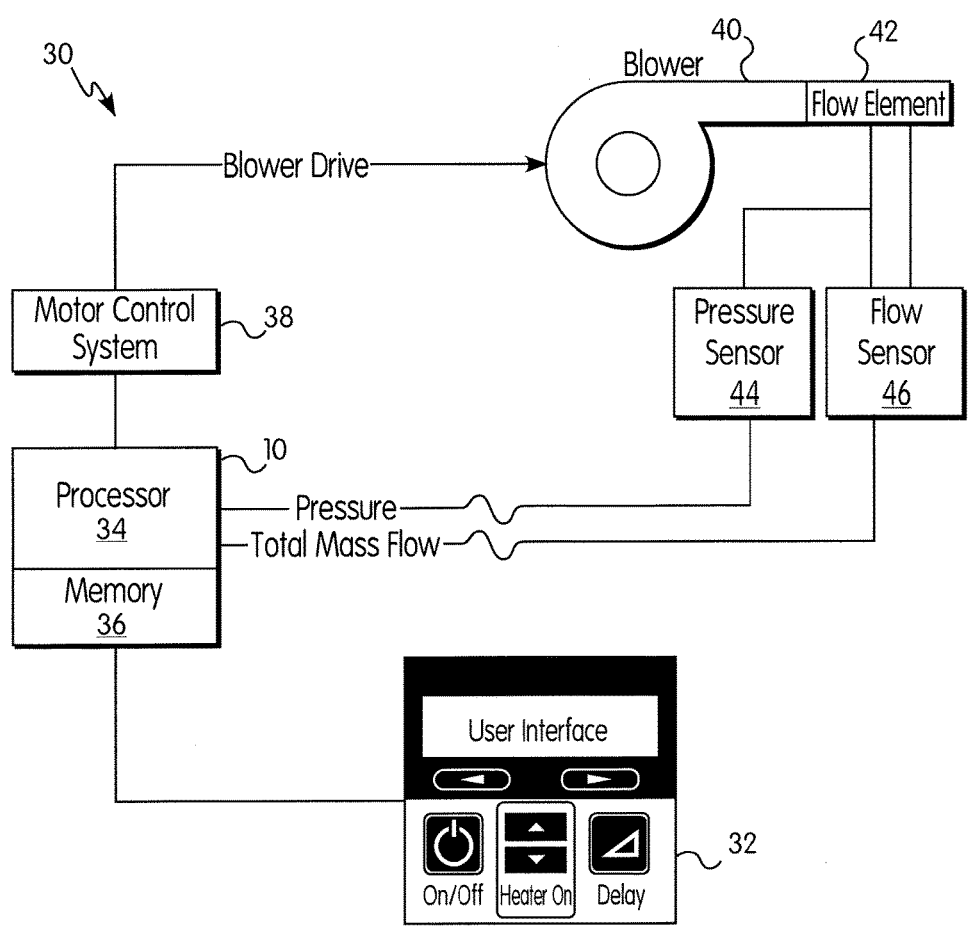
FIG. 1 shows a prior art CPAP device of the type in which the present invention may be implemented.

The improved flow limitation detection algorithm of the present invention can be implemented in a typical prior art device, as shown in FIG. 1, as a software module stored in memory 36. In the preferred embodiment, the algorithm is essentially two algorithms working concurrently, one to determine if the pressure should be raised, and the other to determine if the pressure should be lowered. As one of skill in the art would realize, this is only one way of implementing the invention, and other implementations may be used without deviating from the spirit or scope of the invention. As would also be realized by one of skill in the art, the existence of the flow limitation condition is but one of many factors that can be used in determining the correct setting of the therapeutic pressure. As such, the output of the flow limitation algorithm, in a typical embodiment of a CPAP machine, will be used as one factor among several others to dynamically adjust the therapeutic pressure delivered to the patient.

Figure 3:
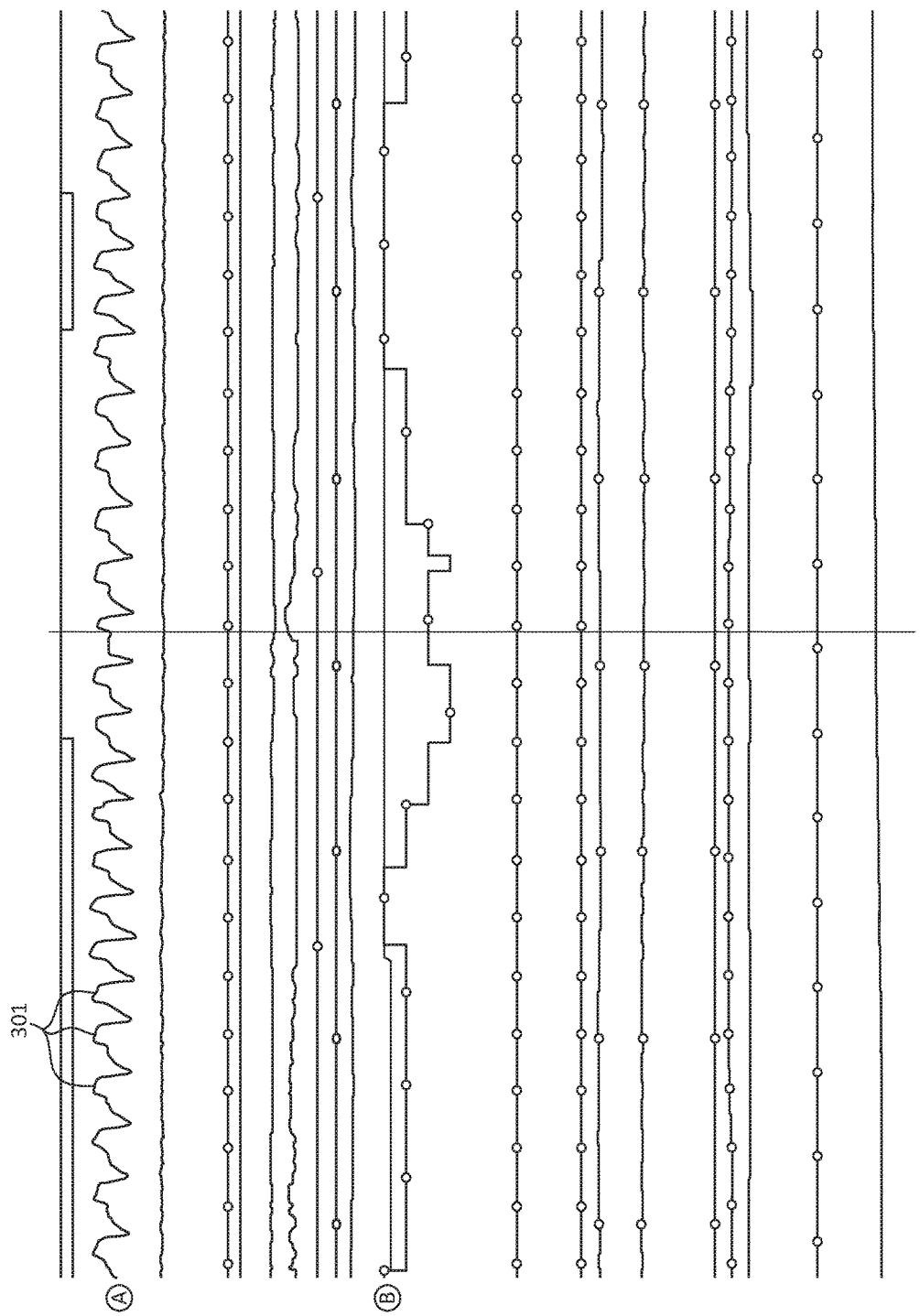
FIG. 3 is a graph showing an airflow waveform exhibiting the flow limitation condition, as well as a waveform showing the output of the flow limitation detection algorithm.
Figure 3:
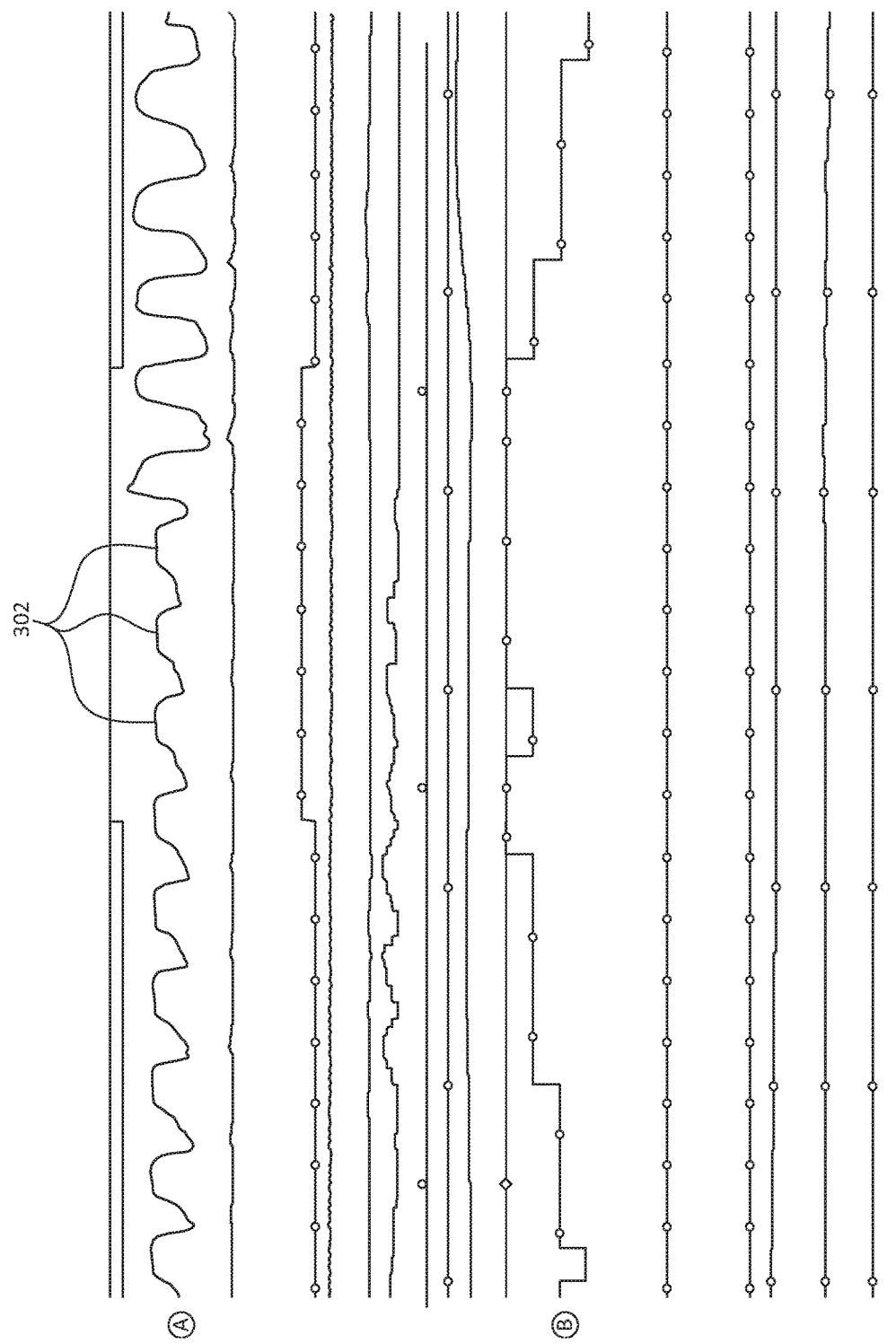

In FIG. 3, reference A shows an airflow waveform displaying the flow limitation condition. The inspiration portion of the breathing cycle is shown above the dotted line. Absent the flow limitation condition, the airflow waveform resembles a sine wave. Visually, the flow limitation condition is easy to detect, being indicated by flattened areas on the inspiration portion of the airflow waveform, examples of which are shown with reference number 301 in FIG. 3, reference A. Note that the flattened areas of the waveform indicative of the flow limitation condition may have a positive or negative slope. The algorithm of the present invention is capable of recognizing both negatively sloped plateaus, as shown by reference number 301, and positively sloped plateaus, as shown by reference number 302.

Figure 2:
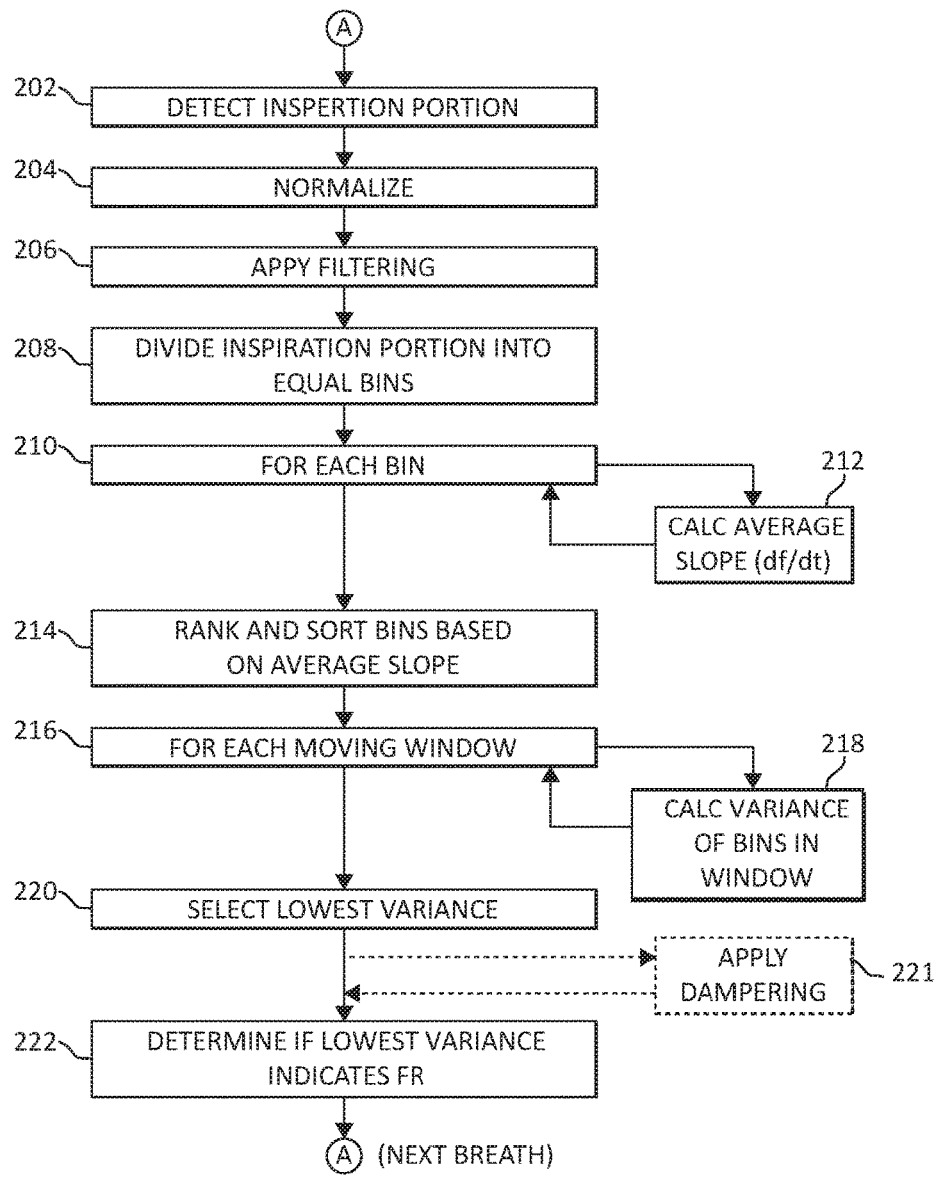
FIG. 2 is a flow chart showing the algorithm used to detect the flow limitation condition.

FIG. 2 shows a flow chart of the algorithm used to analyze the airflow waveform for each breath taken by the patient. As previously discussed, only the inspiration portion of the airflow waveform is of interest in detecting the flow limitation condition.

The algorithm starts at Reference A in FIG. 2 and, in box 202, the inspiration portion of the airflow waveform is detected and its duration is measured. The airflow waveform consists of data points sampled from the flow sensor 46 shown in FIG. 1, which is typically sampled at a rate of 32 Hz. Other sampling rates will, or course, work equally as well. Depending upon the duration of the patient's breathing cycle, the inspiration portion of the airflow waveform could contain from several dozen to several hundred sampled points. In the preferred embodiment, the sampled points are retrieved and stored in an array for processing. Analysis is performed on the inspiration portion of each breathing cycle independently from other breathing cycles.

Once the data from the inhalation portion of the breathing cycle has been obtained and the duration measured, the data is normalized. Because not all breaths taken by the patient are the same (i.e., some breaths may be more or less shallow than others) the breathing sample is normalized in box 204 to an arbitrary standard breath. As one of skill in the art would realize, many methods of normalizing the data can be used. However, in the preferred embodiment of the invention, the average of the airflow signal is taken over the inspiration portion of the breathing cycle, that is, the amplitude of each sampled data point is summed and the sum is divided by the total number of sampled data points. A gain is then applied to each sampled data point based on the calculated average to provide the normalization to the arbitrary standard breath.

In box 206, filtering is applied to smooth the airflow waveform to eliminate small "bumps" in the waveform that have no impact on the overall detection of the flow limitation condition. As one of skill in the art would realize, many forms of filtering may be utilized. However, in the preferred embodiment of the invention, a moving average method is used. A window containing approximately one-ninth of the total number of samples in the inspiration portion of the airflow waveform is averaged, and the window is then shifted by one data point. In the moving average method of filtering, the number of samples contained in the moving average window may be varied without deviating from the scope of the invention.

The algorithm then proceeds to box 208, where, in the preferred embodiment, all of the samples in the inspiration portion of the breathing cycle are divided and placed into bins, with each bin containing an approximately equal number of samples. In the preferred embodiment of the invention the total number of samples is divided into a minimum of 7 separate "bins". So, for example, if the inspiration portion of the breathing cycle contained 175 samples, the first 25 samples would be in the first bin, the next 25 samples would be in the second bin, and so forth. Note that the number of bins chosen is arbitrary and in the preferred embodiment, is nominally 7 and maybe more, depending upon the total number of sampled data points in the inspiration portion of the breathing cycle for a particular breath. As one of skill in the art would realize, any number of bins could be utilized. Additionally, because the actual number of sampled data points may not be evenly divided between the number of bins, all bins may not have the exact number of sampled data points therein.

In box 210, the algorithm iterates through each bin and, in box 212, calculates the average slope over all sampled data points in the bin. Note that the average slope is the derivative of the airflow waveform. To calculate the average slope, the difference between each adjacent pair of sampled data points is taken and summed in an accumulator. When the difference between all points in the bin has been accounted for, the sum is divided by the number of sampled data points in the bin, resulting in the average slope over all sampled data points in the bin. When the average slope has been calculated for each bin, control proceeds to box 214.

In box 214 the bins are numerically ranked and sorted based upon the average slope calculated in box 212. In box 216, a moving window containing 3 bins is iterated over all of the bins and for each window, in box 218, the variance of the average slope of the bins in the window is calculated. As an example, if there are 7 bins, labelled 1, 2, 3, 4, 5, 6 and 7, the variance will be calculated for a moving window containing sets of bins as follows: {1,2,3}, {2,3,4}, {3,4,5}, {4,5,6}, and {5,6,7}. More or less bins may be used, and the number of points over which the variance is calculated may also be varied without departing from the scope of the invention.

Mathematical variance measures how far a set of numbers is spread out. Therefore, a variance of zero indicates that all the values in the calculated set are identical (i.e., they exhibit a steady slope), which would be indicative of a plateaued area of the airflow waveform. A small variance indicates that the data tends to be very close to the mean, and therefore, close to each other, which is indicative of a likelihood of a flow limitation condition, that is, the members of the calculated set where the slope is derived from the airflow waveform are nearly equal, but still show little variation from bin to bin (i.e., a flattened area on the airflow waveform). Simultaneously, the members of the calculated set may exhibit a positive or negative slope. Conversely, a high variance indicates that the data is very spread out around the mean and from each other, which is more indicative of a normal airflow waveform having a high slope variance calculation as measured from all of the calculated sets, and therefore not exhibiting the flow limitation condition.

In box 220 the window having the lowest variance is selected and is analyzed to determine if the value of the variance is indicative of a flow limitation condition.

In box 222 a semi-arbitrary scale is used to determine if a flow limitation condition exists and, if so, if the flow limitation is mild, moderate or severe in nature depending upon the value of the lowest variance for the inspiration portion of each breathing cycle. Control then returns to the beginning of the algorithm for the next breath.

In FIG. 3 the output of the algorithm is shown as Reference B. The waveform in Reference B shows a determination of no flow limitation or a flow limitation characterized as mild, moderate or severe. Note that the determination in waveform B may be offset in time slightly from the airflow waveform A.

One advantage of this invention is that it is detecting what may be perceived as "visual flatness" in the inspiratory airflow waveform, regardless of the slope of the flat portion of the inspiration waveform. It should be noted that flatness is not the equivalent of slope. The detection method of the present invention can detect a "flat" area, even if the slope of the flat area is steep.

One problem with the method of the present invention is that in the presence of ventilation (machines providing bi-level therapy and, in some cases, machines that adjust the pressure in response to events), the airflow waveform tends to be distorted when the pressure is switched from the inhalation pressure to the exhalation pressure, making it have more "flatness" because of the bi-level pressures. It has been found that this distortion almost always co-exists with a very steep slope in the airflow waveform, but is not indicative of the flow limitation condition. As such, the present invention offers an additional embodiment wherein flattened areas of the inspiration airflow waveform having a very steep slope are dampened to reduce the sensitivity to these regions, to avoid falsely determining a flow limitation condition.

In box 221, a dampening factor is applied to the variance based on the average slope, such that the higher the average slope gets, the less of a factor the variance has in the determination of the flow limitation condition. To apply the dampening factor, the average slope of the three bins in the variance window is calculated. A linear or non-linear having the average slope as it's input may be applied to perform the dampening, such that the steeper the slope, the larger the dampening factor for the variance. The variance is multiplied by the dampening factor, such that a large slope will result in a large dampening factor, increasing the variance and making it less likely to be indicative of a flow limitation condition. Many such schemes are possible to make it less likely that a small variance indicates a likelihood of a flow limitation condition when a large slope is also present. All such schemes are intended to be within the scope of the invention.

Once it has been determined that a flow limitation exists, the CPAP machine may make decisions regarding the change in therapeutic pressure delivered to the patient based upon the output of the algorithm. For example, in the preferred embodiment the pressure is increased if a moderate or severe flow limitation is detected for 15 or more seconds in a one-minute period. In such cases, the pressure would rise slightly, for example by 0.2 cmH$_2$O. It is also possible that the CPAP machine would ignore the output of the flow limitation algorithm. For example, if it is observed that raising the pressure several times does not alleviate the flow limitation condition, this may be considered a stable condition for the patient and the raising of the pressure is curtailed to avoid unnecessarily arousing the patient.

In a second embodiment of the invention, the detection of a flow limitation condition may be bolstered with a degree of certainty by applying an analysis of the duty cycle kinetics of the airflow waveform. It has been discovered that a duty cycle in which the inspiration portion is increasing compared to the expiration portion is indicative of the flow limitation condition. This occurs because when airflow is restricted during inspiration, the patient requires more time to get the required volume of air into the lungs and thus the inspiration portion of the duty cycle is increased. A trend over several breaths showing an increase in the percentage of time of the duty cycle spent in inspiration is therefore a strong indicator, especially when combined with the output of the variance-based algorithm of the present invention, that a flow limitation condition exists. As such, an analysis of the duty cycle kinetics may be utilized as a secondary indicator or as a confirmatory degree of certainty when used in conjunction with the flattening detection algorithm. In an alternative second embodiment, a flow limitation condition may only be determined when confirmed by an upwardly trending ratio of inspiration to expiration.

A description of the invention has been provided utilizing specific numbers and examples of calculations. As one of skill in the art would realize there may be other methods to, for example, provide filtering and/or normalization of the data that do not deviate from the intended scope of the invention, which is outlined in the claims which follow.

We claim:

1. A breathing therapy machine having an optimized auto-adjust capability comprising:
   a. a blower, for delivering air to a user of said device at a pressure;
   b. a processor, for controlling said blower;
   c. non-volatile memory, accessible by said processor, said non-volatile memory including operational programming;
   d. an airflow sensor, electrically connected to said processor for gathering data regarding a volume of airflow to said patient, said operational programming producing an airflow waveform from said gathered data; and
   e. a flow limitation detection module, stored in said non-volatile memory as part of said operational programming, wherein said flow limitation detection module is configured to detect a flow limitation condition by:
      grouping data points sampled from an inspiration portion of the airflow waveform into a plurality of bins;
      for each bin, calculating an average slope value using the data points within the bin;
      computing a plurality of variance values, wherein each variance value is computed by defining a moving window that utilizes average slope values calculated for at least three of the bins; and
      selecting and analyzing a lowest variance value of the plurality of variance values to determine if the flow limitation condition exists;
   wherein said pressure of said air is altered based on detection of the flow limitation condition.

2. The breathing therapy machine of claim 1 wherein said airflow waveform consists of a series of breaths, each breath consisting of an inspiration portion and an expiration portion, and further wherein said flow limitation module performs, for each of said breaths, a series of functions including:

detecting a start and end of said inspiration portion of said breath and measuring a duration of said inspiration portion; and selecting the lowest variance value and comparing to a scale to determine if the flow limitation condition is present.

3. The breathing therapy machine of claim 2 wherein said flow limitation module is further configured to perform a function of normalizing the inspiration portion prior to computing the plurality of variance values.

4. The breathing therapy machine of claim 3 wherein said normalization function comprises:

calculating an average flow signal for said inspiration portion; and applying a gain to said inspiration portion based on a comparison of said average flow signal to an arbitrary standard flow signal.

5. The breathing therapy machine of claim 2 wherein said flow limitation module is further configured to perform a function of applying adaptive filtering to smooth said inspiration portion of said airflow waveform portion prior to computing the plurality of variance values.

6. The breathing therapy machine of claim 5 wherein said adaptive filtering function comprises calculating a moving average of said inspiration portion.

7. The breathing therapy machine of claim 6 wherein said moving average is calculated using a window size encompassing approximately $1/9^{th}$ of said inspiration portion.

8. The breathing therapy machine of claim 2 wherein said flow limitation module is further configured to perform a function of ranking and sorting said plurality of bins, each of which corresponds to the data points sampled from an inspiration portion of the airflow waveform, based on said average slope values prior to performing said variance calculations.

9. The breathing therapy machine of claim 2 wherein said function of selecting the lowest of said variance calculations and comparing to the scale to determine if a flow limitation condition is present further comprises assigning a severity of said flow limitation condition based on the lowest variance value.

10. The breathing therapy machine of claim 9 wherein said severity of said flow limitation is selected from a group consisting of none, mild, moderate and severe.

11. The breathing therapy machine of claim 1 wherein said flow limitation detection module is further configured to perform functions comprising:

calculating a ratio of said inspiration portion to said expiration portion for each breath over several breaths; and determining if said ratio is trending toward longer inspiration times and shorter expiration times, and, if so, utilizing said trend as confirmation of the flow limitation condition.

12. The breathing therapy machine of claim 1 wherein said flow limitation detection module is further configured to perform functions comprising:

calculating a ratio of said inspiration portion to said expiration portion for each breath over several breaths; and determining if the flow limitation condition exists only if indicated by said calculation of said variance based on the variance values and trending information associated with said ratio.

13. The breathing therapy machine of claim 1 wherein said pressure is raised if the flow limitation condition is determined to be present for at least 15 seconds in a one minute window.

14. The breathing therapy machine of claim 1 wherein said pressure is periodically raised if the flow limitation condition is determined to be present until a certain predetermined pressure is reached, at which time the flow limitation condition is ignored.

15. The breathing therapy machine of claim 2 wherein a dampening factor is applied to each variance calculation prior to the step of selecting the lowest variance value.

16. The breathing therapy machine of claim 15 wherein a polynomial having the average slope value as an input is used to dampen the variance.

17. The breathing therapy machine of claim 15 wherein said dampening factor lessens an effect of said variance values as the average slope increases.

18. A breathing therapy machine comprising:

a blower, for delivering air to a user of said device at a pressure;

a processor, for controlling said blower;

non-volatile memory, accessible by said processor, said non-volatile memory including operational programming;

an airflow sensor configured to gather airflow data indicating a volume of airflow that is provided to a patient, wherein said operational programming is configured to produce an airflow waveform based on the gathered airflow data; and a flow limitation detection module, stored in said non-volatile memory as part of said operational programming, wherein said flow limitation detection module is configured to detect a flow limitation condition by:

grouping data points sampled from an inspiration portion of the airflow waveform into a plurality of bins;

calculating average slope values for each of the plurality of bins using the data points within the plurality of bins;

numerically ranking and sorting said plurality of bins based upon the average slopes calculated for the plurality of bins;

computing a plurality of variance values using a moving window that iterates over the plurality of bins after the plurality of bins have been numerically ranked and sorted, wherein each variance value is computed using the moving window to identify at least three consecutive bins and to compute a variance of the average slope values associated with the three consecutive bins identified in the moving window;

selecting a lowest variance value from the plurality of computed variance values; and analyzing the lowest variance value to determine if the flow limitation condition exists;

wherein the breathing therapy machine alters said pressure of said air in response to detecting the flow limitation condition.

* * * * *